United States Patent
Cukrowski

(10) Patent No.: US 7,081,134 B2
(45) Date of Patent: Jul. 25, 2006

(54) POSTERIOR CHAMBER LENS IMPLANT

(76) Inventor: Walter Cukrowski, 2139 Windemere, Birmingham, MI (US) 48009

( * ) Notice: Subject to any disclaimer, the term of this patent is extended or adjusted under 35 U.S.C. 154(b) by 26 days.

(21) Appl. No.: 10/741,267

(22) Filed: Dec. 19, 2003

(65) Prior Publication Data

US 2005/0149185 A1    Jul. 7, 2005

(51) Int. Cl.
*A61F 2/16* (2006.01)
(52) U.S. Cl. ..................... 623/6.34; 623/6.38
(58) Field of Classification Search ...... 623/6.33–6.39, 623/6.43–6.49
See application file for complete search history.

(56) References Cited

U.S. PATENT DOCUMENTS

| | | | | |
|---|---|---|---|---|
| 5,607,472 A | * | 3/1997 | Thompson | 623/6.13 |
| 5,876,442 A | * | 3/1999 | Lipshitz et al. | 623/6.34 |
| 6,113,633 A | * | 9/2000 | Portney | 623/6.32 |
| 6,197,058 B1 | * | 3/2001 | Portney | 623/6.34 |
| 6,280,471 B1 | * | 8/2001 | Peyman et al. | 623/6.17 |
| 6,488,708 B1 | * | 12/2002 | Sarfarazi | 623/6.34 |
| 6,558,420 B1 | * | 5/2003 | Green | 623/6.34 |
| 2004/0082994 A1 | * | 4/2004 | Woods et al. | 623/6.34 |
| 2004/0169816 A1 | * | 9/2004 | Esch | 351/160 R |
| 2005/0267575 A1 | * | 12/2005 | Nguyen et al. | 623/6.34 |
| 2006/0069431 A1 | * | 3/2006 | Graney et al. | 623/6.34 |

* cited by examiner

*Primary Examiner*—Suzette J-J Gherbi
(74) *Attorney, Agent, or Firm*—Gifford, Krass, Groh, Sprinkle, Anderson & Citkowski, P.C.

(57) ABSTRACT

A posterior chamber lens implant for use after extracapsular surgery. The lens implant includes a first lens having a predetermined refractive power and a second lens having a second predetermined refractive power. A support structure maintains the first and second lenses in a spaced apart relationship relative to each other. The lens implant achieves both near and far vision.

16 Claims, 2 Drawing Sheets

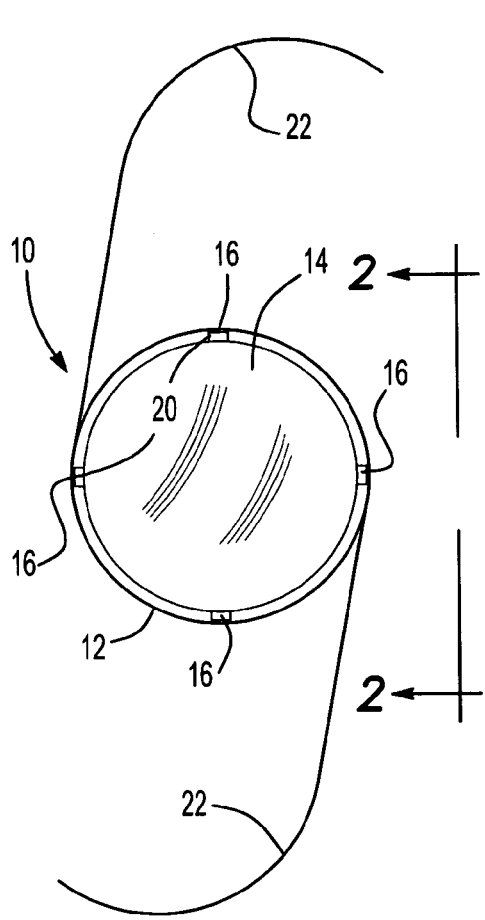
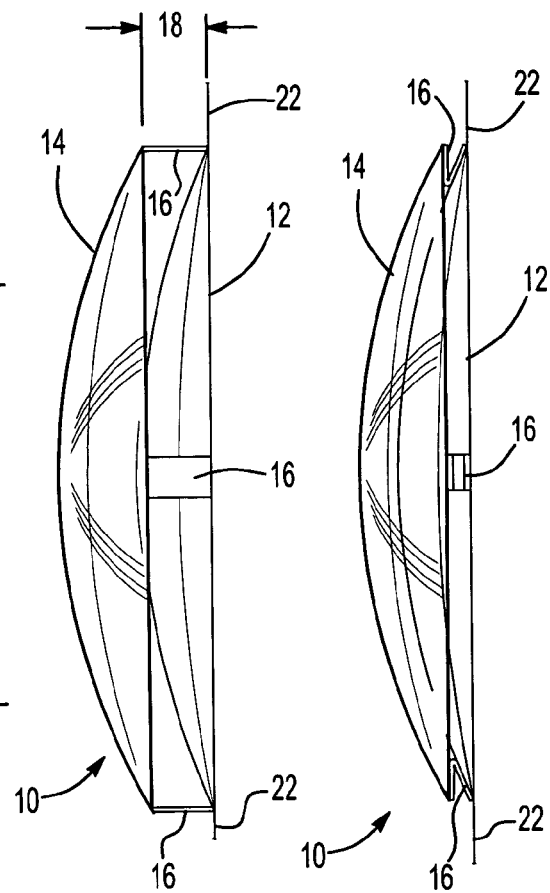
Fig-1          Fig-2          Fig-3
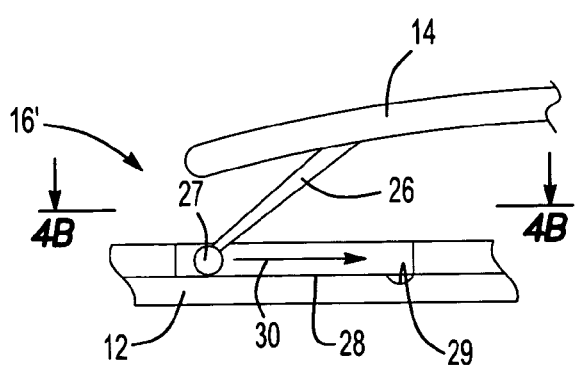
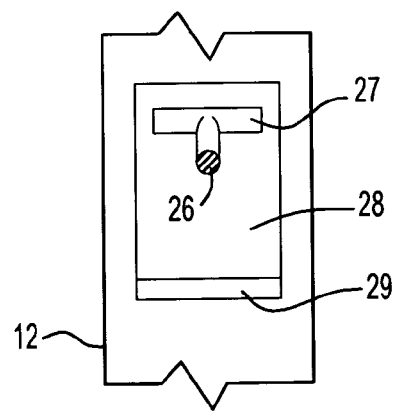
Fig-4A         Fig-4B

POSTERIOR CHAMBER LENS IMPLANT

BACKGROUND OF THE INVENTION

I. Field of the Invention

The present invention relates to a posterior chamber implant for use after extracapsular surgery.

II. Description of Related Art

In extracapsular surgery, a surgical opening is formed through the front membrane of the lens of the human eye and the cataracts and the fluids within the interior of the lens are then surgically removed. During such surgery, the posterior capsule of the lens is usually left intact so that it forms a barrier between the vitreous humor and the aqueous humor in the eye.

After removal of the cataracts and other material within the original lens, it is necessary to replace the eye lens with an artificial lens implant in order to restore sight to the eye. Although such artificial lenses have in the past been placed in the anterior chamber, it has been found that placement of the artificial lens in the posterior chamber, i.e. in the lens sack, is superior for many reasons.

These previously known posterior chamber lens implants typically comprise a lens having a convex front surface and a planar or concave rear surface. Two or more haptics are then secured to the lens in order to center and attach the lens in the lens sack.

A primary disadvantage of many of these previously known posterior chamber lens implants, however, is that such lens implants are only capable of restoring far vision for the patient, especially when the patient is of middle age or older. For such patients, the previously known posterior chamber lens implants do not restore near vision of the type necessary for reading. Consequently, patients who have undergone lens implantation surgery must still wear reading glasses to read even though their far vision is restored.

There have, however, been attempts at the multi-focal lens implants, i.e. lens implants that would restore both far and near vision. In one such previously known multi-focal lens, concentric rings are formed on the lens to achieve both near and far vision.

A primary disadvantage, however, of these previously known multi-focal lenses is that such lenses are particularly susceptible to glare, particularly at night. Consequently, such multi-focal lenses have not achieved widespread use or acceptance.

SUMMARY OF THE PRESENT INVENTION

The present invention provides a multi-focal posterior chamber lens implant which overcomes all of the above-mentioned disadvantages of the previously known implants.

In brief, the lens implant of the present invention comprises a first lens having a first predetermined refractive power. This first lens preferably has a refractive power in the range of 15–25 diopters.

The lens implant further comprises a second lens having a second predetermined refractive power. Preferably, the refractive power of the second lens is in the range of 0.1–10 diopters.

A support structure then secures the first and second lenses together so that the first and second lens are in a spaced apart relationship relative to each other. Upon insertion into the posterior chamber, both lenses are aligned with the iris of the eye with the first lens position posteriorly of the second lens.

The first and second lenses may be made of any conventional material such as silicone, acrylic, PMMA and the like. Furthermore, although the lens material for both the first and second lenses may be flexible to facilitate insertion of the lens implant into the posterior chamber, once the lens implant is implanted into the posterior chamber, the first and second lens retain a fixed shape and spacing relative to each other. Furthermore, any conventional means, such as haptics, are preferably employed to both center and attach the lens implant in the posterior chamber.

In practice, the combination of the first and second lenses provide both near and far vision for the patient.

BRIEF DESCRIPTION OF THE DRAWING

A better understanding of the present invention will be had upon reference to the following detailed description, when read in conjunction with the accompanying drawing, wherein like reference characters refer to like parts throughout the several views, and in which:

FIG. 1 is a front view illustrating a preferred embodiment of the prevent invention;

FIG. 2 is a side view taken substantially along line 2—2 in FIG. 1;

FIG. 3 is a view similar to FIG. 2, but illustrating the first and second lenses compressed together to facilitate insertion of the lens into the posterior chamber;

FIG. 4A is a diagrammatic view illustrating an alternate embodiment of the present invention;

FIG. 4B is a fragmentary partial sectional view taken along line 4B—4B in FIG. 4A;

DETAILED DESCRIPTION OF PREFERRED EMBODIMENTS OF THE PRESENT INVENTION

Figure 5:
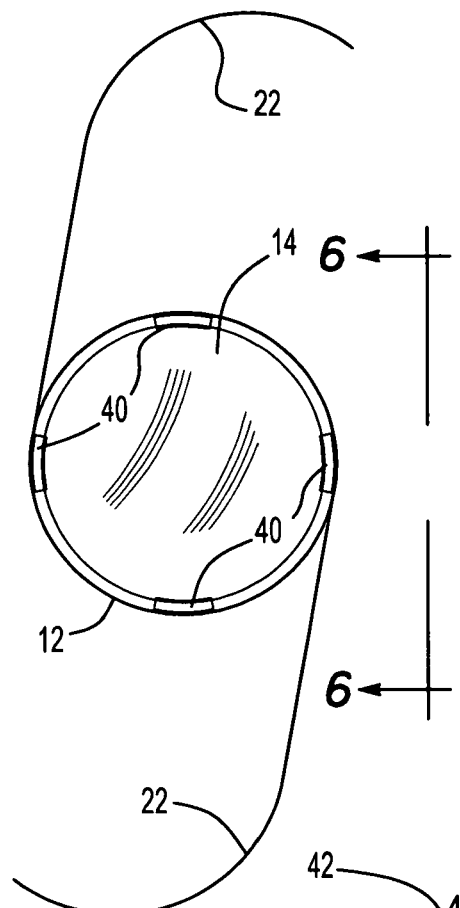
FIG. 5 is a view similar to FIG. 1, but illustrating a third preferred embodiment of the invention.

With reference first to FIGS. 1 and 2, a first preferred embodiment of the posterior chamber lens implant 10 of the present invention is shown and comprises a first lens 12 and a second lens 14. Both lenses 12 and 14 are generally circular in shape as best shown in FIG. 1, with the second lens 14 having either the same or a somewhat smaller diameter than the first lens 12.

The first lens has a refractive power that is greater than the refractive power of the second lens 14. Preferably, the first lens 12 has a refractive power in the range of 15–25 diopters while the second lens 14 has a refractive power in the range of 0.1–10 diopters.

The lenses 12 and 14 may be constructed of any conventional material such a silicone, acrylic, PMMA and the like. Furthermore, even though the lenses 12 and 14 may be constructed of a flexible material to facilitate their insertion into the posterior chamber during surgery, once the lens implant 10 is positioned within the posterior chamber, the lenses 12 and 14 maintain a fixed shape.

Still referring to FIGS. 1 and 2, a support structure 16 maintains a fixed spacing 18 (FIG. 2) between the lenses 12 and 14 following implantation of the lens implant 10 into the posterior chamber. Although the support structure 16 may take any shape or form as illustrated in FIGS. 1 and 2, a support structure 16 comprises a plurality of circumferentially spaced legs 20 extending between and secured to the lenses 12 and 14.

With reference now to FIGS. 2 and 3, the support structure 16 is preferably formed of a collapsible material, such as silicone, so that the lenses 12 and 14 may be compressed together as shown in FIG. 3. Such compression of the support structure 16 facilitates the insertion of the implant 10 into the posterior chamber by minimizing the required incision size. Furthermore, if the lenses 12 and 14 are made of a flexible material, the lens implant may be folded to facilitate injection of the lens implant 10 into the eye. However, once the lens implant 10 is positioned within the posterior chamber after extra capsular surgery, the support structure 16 returns to its extended position, illustrated in FIG. 2, so that the space in between the first lens 12 and second lens 14 remains fixed following implantation.

With reference to FIG. 1, any conventional means may be used to center the lens implant 10 within the posterior chamber. For example, haptics 22 may be secured to the first lens 12 in any conventional fashion, such as by staking.

With reference now to FIGS. 4A and 4B, an alternative embodiment for the support structure is shown. In FIGS. 4A and 4B, a support structure 16' includes a plurality of circumferentially spaced slidable legs 26 (only one of which is shown in FIGS. 4A and 4B) having a crossbar 27 at one end. The leg 26 is secured to the outer lens 14 at its other end but the crossbar 27 is slidably mounted within a channel 28 formed on the first lens 12. Consequently, by displacing the crossbar 27 in the channel as indicated by arrow 30, the second lens 14 is moved from a collapsed position in which the second lens 14 is collapsed onto and closely adjacent the first lens 12, to an extended or operational position. Any conventional means may be used to lock the leg 26 when in its extended position. However, as shown, the crossbar 27 drops into a notch 29 in the channel 28 when the leg 26 is moved to its extended position.

When the lens implant 10 is positioned within the posterior chamber of the eye, the lenses 12 and 14 are aligned with the iris of the eye and thus the line of vision for the eye. In doing so, the first lens 12 is positioned posteriorly relative to the second lens 14.

Figure 6:
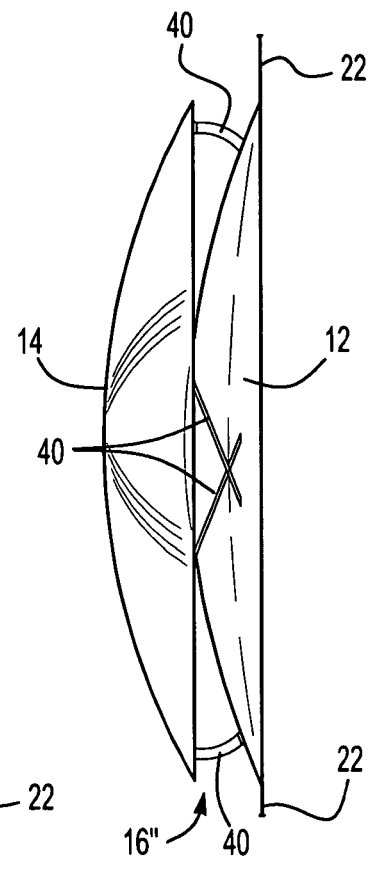
FIG. 6 is a view taken along line 6—6 in FIG. 5.
Figure 7:
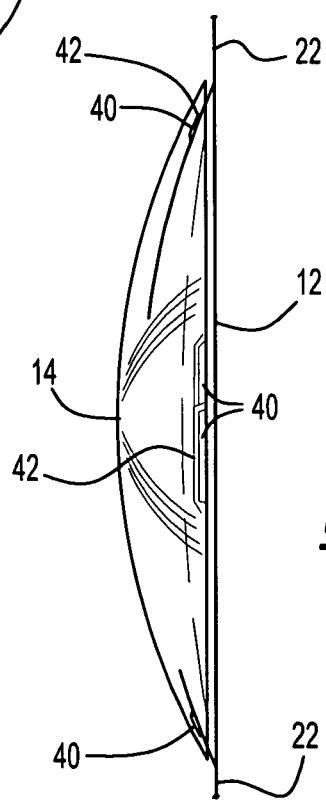
FIG. 7 is a view similar to FIG. 6, but illustrating the lens implant in a compressed condition.

With reference now to FIGS. 5–7 a still further embodiment of the invention is shown in which the support structure 16" comprises a plurality of circumferentially spaced legs 40 which extend between the lenses 12 and 14. Unlike the legs 20 in FIG. 1, however, the legs extend at an oblique angle, best shown in FIG. 6, between the lenses 12 and 14. Additionally, each leg preferable registers with a channel 42 formed around the outer edge of the lens 12 or optionally formed in the lens 14.

Consequently, by slight rotation of the lens 14 relative to the lens 12, the lens implant is movable between a collapsed position, illustrated in FIG. 7, and an operational position, illustrated in FIG. 6. Furthermore, in its collapsed position the legs nest within the channels 42 thus minimizing the thickness of the lens implant to facilitate folding and inserting the implant into the eye.

The provision of the dual lens 12 and 14 following implantation into the posterior chamber restores both near and far vision to the patient without the adverse effects of glare common to the previously known multi-focal lenses. This near and far vision is achieved since the dual lenses 12 and 14 provide two focal points for the eye, one for near and one for far vision. In practice, it is believed that the lens 12 provides far vision while the combined power of the lenses 12 and 14 provide near vision.

Having described my invention, many modifications thereto will become apparent to those skilled in the art to which it pertains without deviation from the spirit of the invention as defined by the scope of the appended claims.

I claim:

1. A posterior chamber lens implant for use after extra-capsular surgery comprising:
   a front first lens having a first predetermined refractive power, said first lens having a convex front surface and a concave rear surface,
   a rear second lens having a second predetermined refractive power, said second lens having a convex front surface facing and nestable within said rear surface of said first lens,
   a support structure which maintains said rear surface of said first lens and said front surface of said second lens in a spaced apart and axially aligned relationship with respect to each other, said support structure comprises a plurality of support legs extending between and secured to said lenses, said support legs being circumferentially spaced from each other and wholly positioned within an outer perimeter of both of said lenses, said legs allowing compression of said first and second lenses together so that, upon compression of said lenses together, said second lens rests within said first lens, said support legs are sandwiched between said first and second lenses.

2. The invention as defined in claim 1 wherein said support structure comprises at least one leg extending between and secured to said first and second lenses.

3. The invention as defined in claim 2 wherein said at least one leg extends at an oblique angle between said first and second lenses.

4. The invention as defined in claim 3 wherein one of said lenses includes at least one circumferentially extending channel around and outer edge and wherein said at least one leg rests in said at least one channel when said lenses are compressed together.

5. The invention as defined in claim 1 wherein said support structure is made of a compressible material so that, upon compression, said rear surface of said first lens and said front surface of said second lens are closely adjacent each other.

6. The invention as defined in claim 5 wherein said support structure comprises silicone.

7. The invention as defined in claim 1 wherein at least one of said lenses is made of silicone.

8. The invention as defined in claim 1 wherein at least one of said lenses is made of PMMA.

9. The invention as defined in claim 1 wherein at least one of said lenses is made of acrylic.

10. The invention as defined in claim 1 wherein said first lens has a refractive power of less than ten.

11. The invention as defined in claim 10 wherein said second lens has a refractive power of greater than fifteen.

12. The invention as defined in claim 1 wherein said lenses are made of a material such that, after implantation, said lenses both maintain a rigid shape.

13. The invention as defined in claim 1 wherein both lenses are circular in shape.

14. The invention as defined in claim 1 wherein said legs comprise a compressible material.

15. The invention as defined in claim 14 wherein said legs comprise silicone.

16. A posterior chamber lens implant for use after extra-capsular surgery comprising:
    a first lens having a first predetermined refractive power, a second lens having a second predetermined refractive power, a support structure which maintains said first and second lens in a spaced apart relationship with respect to each other, wherein said support structure comprises at least one leg extending between and secured to said first and second lenses, wherein said at least one leg extends at an oblique angle between said first and second lenses, and wherein one of said lenses includes at least one circumferentially extending channel around and outer edge and wherein said at least one leg rests in said at least one channel when said lenses are compressed together.

* * * * *